US011883685B2

(12) United States Patent
Ni et al.

(10) Patent No.: US 11,883,685 B2
(45) Date of Patent: Jan. 30, 2024

(54) THERAPEUTIC SYSTEM AND METHOD

(71) Applicant: SHANGHAI UNITED IMAGING HEALTHCARE CO., LTD., Shanghai (CN)

(72) Inventors: Cheng Ni, Shanghai (CN); Jianfeng Liu, Shanghai (CN); Xingen Yu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 348 days.

(21) Appl. No.: 17/182,228

(22) Filed: Feb. 22, 2021

(65) Prior Publication Data

US 2021/0170197 A1    Jun. 10, 2021

Related U.S. Application Data

(63) Continuation-in-part of application No. 16/792,418, filed on Feb. 17, 2020, now Pat. No. 10,926,107, which is a continuation of application No. 15/689,040, filed on Aug. 29, 2017, now Pat. No. 10,561,859.

(30) Foreign Application Priority Data

Aug. 24, 2017  (CN) .......................... 201710737272.3

(51) Int. Cl.
*A61N 5/10*   (2006.01)
*A61N 5/06*   (2006.01)

(52) U.S. Cl.
CPC ......... *A61N 5/1039* (2013.01); *A61N 5/1042* (2013.01); *A61N 5/1049* (2013.01); *A61N 5/1064* (2013.01); *A61N 2005/0642* (2013.01); *A61N 2005/1052* (2013.01); *A61N 2005/1055* (2013.01)

(58) Field of Classification Search
CPC .. A61N 5/1039; A61N 5/1042; A61N 5/1049; A61N 5/1064; A61N 2005/0642; A61N 2005/1052; A61N 2005/1055
See application file for complete search history.

(56) References Cited

U.S. PATENT DOCUMENTS

| 6,512,813 | B1 | 1/2003 | Krispel et al. |
| 10,561,859 | B2 | 2/2020 | Ni et al. |
| 2001/0001807 | A1 | 5/2001 | Green |
| 2001/0049475 | A1 | 12/2001 | Bucholz et al. |
| 2002/0091314 | A1 | 7/2002 | Schlossbauer et al. |
| 2002/0151786 | A1 | 10/2002 | Shukla et al. |
| 2007/0135703 | A1 | 6/2007 | Rietzel et al. |
| 2007/0244386 | A1 | 10/2007 | Steckner et al. |

(Continued)

FOREIGN PATENT DOCUMENTS

| CN | 105233425 A | 1/2016 |
| WO | 2015044239 A1 | 4/2015 |

(Continued)

*Primary Examiner* — Mark R Gaworecki
(74) *Attorney, Agent, or Firm* — METIS IP LLC

(57) ABSTRACT

The present disclosure relates to a system and a method. The system may include a first device including a treatment head configured to emit a radiation beam. The system may include a second device comprising a body. The body may include one or more openings at a bottom of the recess that allow passage of the radiation beam substantially free of the interference by the body.

20 Claims, 11 Drawing Sheets

(56) References Cited

U.S. PATENT DOCUMENTS

| | | |
|---|---|---|
| 2009/0124887 A1 | 5/2009 | Roell et al. |
| 2009/0299170 A1 | 12/2009 | Gebhardt et al. |
| 2010/0049030 A1 | 2/2010 | Saunders et al. |
| 2010/0174172 A1 | 7/2010 | Ein-Gal |
| 2010/0185080 A1 | 7/2010 | Myhr |
| 2010/0239066 A1 | 9/2010 | Fahrig et al. |
| 2010/0329414 A1 | 12/2010 | Zhu et al. |
| 2011/0213239 A1 | 9/2011 | Amies et al. |
| 2012/0008744 A1 | 1/2012 | Bani-Hashemi |
| 2012/0189102 A1 | 7/2012 | Maurer, Jr. et al. |
| 2013/0225975 A1 | 8/2013 | Harvey |
| 2014/0135615 A1 | 5/2014 | Kruip |
| 2016/0136456 A1 | 5/2016 | Jonas et al. |
| 2016/0356869 A1 | 12/2016 | Dempsey et al. |

FOREIGN PATENT DOCUMENTS

| | | |
|---|---|---|
| WO | 2015050527 A1 | 4/2015 |
| WO | 2015103184 A1 | 7/2015 |
| WO | 2015135825 A1 | 9/2015 |
| WO | 2015144540 A1 | 10/2015 |
| WO | 2015150065 A1 | 10/2015 |
| WO | 2015150575 A1 | 10/2015 |
| WO | 2016014695 A2 | 1/2016 |
| WO | 2016034364 A1 | 3/2016 |
| WO | 2016034568 A1 | 3/2016 |
| WO | 2016071733 A1 | 5/2016 |

THERAPEUTIC SYSTEM AND METHOD

CROSS-REFERENCE TO RELATED APPLICATIONS

This application is a continuation-in-part of U.S. patent application Ser. No. 16/792,418, filed on Feb. 17, 2020, which is a continuation application of U.S. patent application Ser. No. 15/689,040 (now U.S. Pat. No. 10,561,859), filed on Aug. 29, 2017, which in turn claims priority of Chinese Patent Application No. 201710737272.3 filed on Aug. 24, 2017. The entire contents of each of the above-identified applications are hereby incorporated by reference.

TECHNICAL HELD

The present disclosure generally relates to a therapeutic system, and more particularly, relates to an image-guided radiotherapy system which combines radiotherapy and magnetic resonance imaging technique.

BACKGROUND

Radiation therapy of a tumor is currently limited by the inability to follow the motion of the tumor during treatment. Magnetic resonance imaging (MRI) technique has the potential to provide good images of the tumor, fast enough to allow imaging during treatment. This would allow accurate dose deposition in the tumor and spare the surrounding tissue. Integration of MRI and Linear Accelerators (LINAC) opens new horizons in radiotherapy by improved lesion targeting, especially for moving organs. It may be desirable to provide systems for enhancing therapeutic efficiency with MRI technique.

SUMMARY

According to an aspect of the present disclosure, a system is provided. The system may include a first device including a treatment head configured to emit a treatment beam. The system may include a second device comprising a body. The body may include one or more openings that allow passage of the treatment beam substantially free of the interference by the body.

According to another aspect of the present disclosure, a method is provided. The method may be implemented using a system including a first device and a second device. The first device may include a treatment head configured to emit a treatment beam. The second device may include a body. The body may include one or more openings that allow passage of the treatment beam substantially free of the interference by the body. The method may include determining a position of a treatment region. The method may include determining the position of the treatment region is within a preset range. The method may further include causing the treatment head to emit the treatment beam toward the treatment region.

In some embodiments, the body may further include a recess on an outer wall of the body for accommodating at least a portion of the treatment head, and the more or more openings may be at a bottom of the recess.

In some embodiments, the system may further include a controller configured to rotate the treatment head around the recess and locate the treatment head at one or more positions corresponding to the one or more openings.

In some embodiments, the controller may match an axis of the treatment head to the axis of an opening of the one or more openings at the bottom of the recess.

In some embodiments, a depth of the recess may be determined according to an external diameter of the body, an inner diameter of the body, and an irradiating distance of the treatment head.

In some embodiments, the irradiating distance may relate to a distance between an end face of the treatment head and an axis of the body.

In some embodiments, the irradiating distance may range from 40 centimeters to 50 centimeters.

In some embodiments, the depth of the recess may be no less than 50 centimeters.

In some embodiments, a depth of at least one of the one or more openings may be determined according to the external diameter of the body, the inner diameter of the body, and the depth of the recess.

In some embodiments, a width of the recess may be greater than a width of an opening of the one or more openings at the bottom of the recess.

In some embodiments, the one or more openings may be uniformly distributed along the recess.

In some embodiments, an angle between axes of two adjacent openings of the one or more openings may be 180 degrees, 120 degrees, 90 degrees, 60 degrees, or 30 degrees.

In some embodiments, shapes of the one or more openings may include at least one of a rectangle, a rounded rectangle, a circle, an ellipse, a rhombus, a polygon, or a rounded polygon.

In some embodiments, at least one of the one or more openings may correspond to an arc of a circumference of the recess.

In some embodiments, the arc may range from $1/10\pi$ radians to $3/2\pi$ radians.

In some embodiments, at least one of the one or more openings may be a through hole.

In some embodiments, the at least one of the one or more openings may be filled up by a material that is at least partially radiation transparent.

In some embodiments, the first device may include a radiotherapy device.

In some embodiments, the second device may include a magnetic resonance imaging device, and the body may include a magnetic body configured to generate a magnetic field.

In some embodiments, the magnetic body may further include one or more main cons that are electrically connected to each other.

In some embodiments, if the position of the treatment region is not within the preset range, the position of the treatment region may be adjusted according to the preset range.

In some embodiments, if the position of the treatment region is not within the preset range, an adjusting angle may be determined based on the position of the treatment region, and the treatment head may rotate according to the adjusting angle.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is for the purpose of describing particular exemplary embodiments only and is not intended to be limiting. As used herein, the singular forms "a" "an," and "the" may be intended to include the plural forms as well, unless the context dearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of the present disclosure. It is to be expressly understood, however, that the drawings are for the purpose of illustration and description only and are not intended to limit the scope of the present disclosure. It is understood that the drawings are not to scale.

Figure 1:
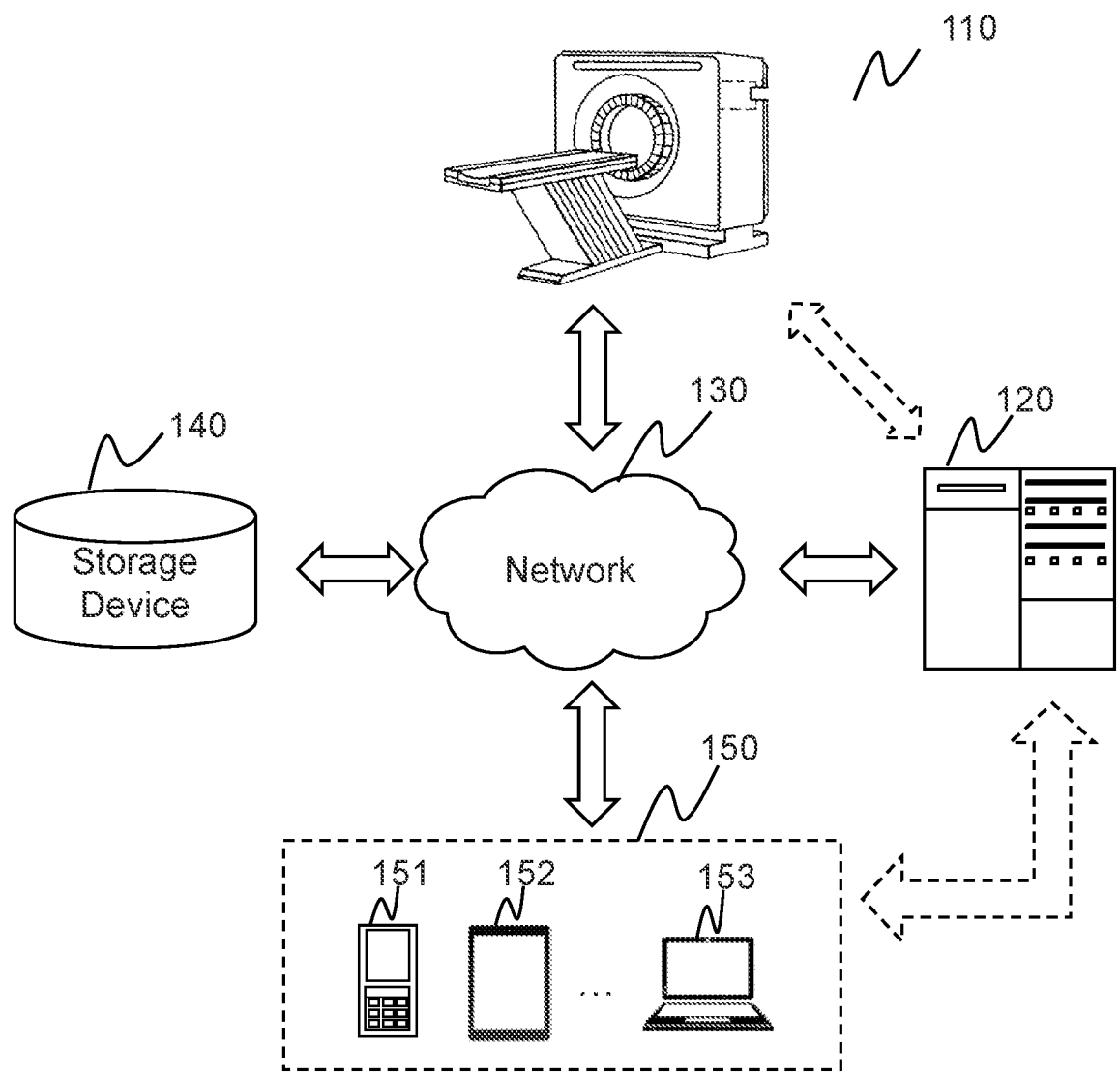
FIG. 1 is a block diagram illustrating an exemplary therapeutic system according to some embodiments of the present disclosure.

FIG. 1 is a block diagram illustrating an exemplary therapeutic system 100 according to some embodiments of the present disclosure. The therapeutic system 100 may be a single modality imaging system including, for example, a digital subtraction angiography (DSA) system, a magnetic resonance imaging (MRI) system, a radiotherapy (RT) system, a computed tomography angiography (CTA) system, a positron emission tomography (PET) system, a single photon emission computed tomography (SPECT) system, a computed tomography (CT) system, a digital radiography (DR) system, etc. In some embodiments, the therapeutic system 100 may be a multi-modality imaging system including, for example, a positron emission tomography-computed tomography (PET-CT) system, a positron emission tomography-magnetic resonance imaging (PET-MRI) system, a positron emission tomography-radiotherapy (PET-RT) system, a magnetic resonance imaging-radiotherapy (MRI-RT) system, a single photon emission computed tomography-positron emission tomography (SPECT-PET) system, etc. For better understanding the present disclosure, an MRI-RT system may be described as an example of the therapeutic system 100, and not intended to limit the scope of the present disclosure.

As shown in FIG. 1, the therapeutic system 100 may include a therapeutic apparatus 110, a processing engine 120, a network 130, a storage device 140, and one or more terminal devices 150. In some embodiments, the therapeutic apparatus 110, the processing engine 120, the storage device 140, and/or the terminal device 150 may be connected to and/or communicate with each other via a wireless connection (e.g., the network 130), a wired connection, or any combination thereof.

The therapeutic apparatus 110 may generate image data associated with magnetic resonance signals (hereinafter be referred to as "MR signals") via scanning a subject or a part of the subject. In some embodiments, the subject may include a body, a substance, an object, or the like, or any combination thereof. In some embodiments, the subject may include a specific portion of a body, a specific organ, or a specific tissue, such as head, brain, neck, body, shoulder, arm, thorax, cardiac, stomach, blood vessel, soft tissue, knee, feet, or the like, or any combination thereof. In some embodiments, the therapeutic apparatus 110 may transmit the image data via the network 130 to the processing engine 120, the storage device 140, and/or the terminal device 150. For example, the image data may be sent to the processing engine 120 for further processing, or may be stored in the storage device 140.

In some embodiments, the therapeutic apparatus 110 may provide radiation for tumor treatment. The radiation used herein may include a particle ray, a photon ray, etc. The particle ray may include neutron, proton, electron, μ-meson, heavy ion, or the like, or any combination thereof. The photon ray may include X-ray, γ-ray, α-ray, β-ray, ultraviolet, laser, or the like, or any combination thereof. For illustration purposes, a radiotherapy apparatus associated with X-ray may be described as an example. In some embodiments, the therapeutic apparatus 110 may generate a dose of X-rays to perform radiotherapy under the assistance of image data. For example, the image data may be processed to locate a tumor and/or determine the dose of X-rays.

The processing engine 120 may process data and/or information obtained from the therapeutic apparatus 110, the storage device 140, and/or the terminal device 150. For example, the processing engine 120 may process image data and reconstruct at least one MR image based on the image data. As another example, the processing engine 120 may determine the position of the tumor and the dose of radiation based on the at least one MR image. The MRI image may provide advantages including, for example, superior soft-tissue contrast, high resolution, geometric accuracy, which may allow accurate positioning of the treatment region. For instance, the MRI image may be used to detect the tumor regression or metastasis on the basis of which an original treatment plan may be adjusted accordingly. The original treatment plan may be determined before the treatment commences. For instance, the original treatment plan may be determined at least one day, or three days, or a week, or two weeks; or a month, etc., before the treatment commences. The treatment region may change between when the treatment plan is determined and when the treatment is carried out, which may be detected based on the acquired MR image. In the original or adjusted treatment plan; the dose of radiation may be determined according to, for example, synthetic electron density information. In some embodiments, the synthetic electron density information may be generated based on the MRI image. In some embodiments, the synthetic electron density information may be generated based on the MRI image and another type of image, for example, a CT image. In some embodiments, the processing engine 120 may be a single server or a server group. The server group may be centralized or distributed. In some embodiments, the processing engine 120 may be local or remote. For example, the processing engine 120 may access information and/or data from the therapeutic apparatus 110, the storage device 140, and/or the terminal device 150 via the network 130. As another example; the processing engine 120 may be directly connected to the therapeutic apparatus 110, the terminal device 150, and/or the storage device 140 to access information and/or data. In some embodiments; the processing engine 120 may be implemented on a cloud platform. For example, the cloud platform may include a private cloud, a public cloud, a hybrid cloud, a community cloud, a distributed cloud, an inter-cloud, a multi-cloud, or the like, or any combination thereof.

The network 130 may include any suitable network that can facilitate the exchange of information and/or data for the therapeutic system 100. In some embodiments, one or more components of the therapeutic system 100 (e.g., the therapeutic apparatus 110, the processing engine 120, the storage device 140, or the terminal device 150) may communicate information and/or data with one or more other components of the therapeutic system 100 via the network 130. For example, the processing engine 120 may obtain image data from the therapeutic apparatus 110 via the network 130. As another example, the processing engine 120 may obtain user instructions from the terminal device 150 via the network 130. The network 130 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, or the like, or any combination thereof. In some embodiments, the network 130 may include one or more network access points. For example, the network 130 may include wired and/or wireless network access points such as base stations and/or internet exchange points through which one or more components of the therapeutic system 100 may be connected to the network 130 to exchange data and/or information.

The storage device 140 may store data, instructions, and/or any other information. In some embodiments, the storage device 140 may store data obtained from the processing engine 120 and/or the terminal device 150. In some embodiments, the storage device 140 may store data and/or instructions that the processing engine 120 may execute or use to perform exemplary methods described in the present disclosure. In some embodiments, the storage device 140 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 140 may be implemented on a cloud platform as described elsewhere in the present disclosure.

In some embodiments, the storage device 140 may be connected to the network 130 to communicate with one or more other components of the therapeutic system 100 (e.g., the processing engine 120 or the terminal device 150). One or more components of the therapeutic system 100 may access the data or instructions stored in the storage device 140 via the network 130. In some embodiments, the storage device 140 may be part of the processing engine 120.

The terminal device 150 may be connected to and/or communicate with the therapeutic apparatus 110, the processing engine 120, and/or the storage device 140. For example, the processing engine 120 may acquire a scanning protocol from the terminal device 150. As another example, the terminal device 150 may obtain image data from the therapeutic 110 and/or the storage device 140. In some embodiments, the terminal device 150 may include a mobile device 151, a tablet computer 152, a laptop computer 153, or the like, or any combination thereof. For example, the mobile device 151 may include a mobile phone, a personal digital assistance (FDA), a gaming device, a navigation device, a point of sale (POS) device, a laptop, a tablet computer, a desktop, or the like, or any combination thereof. In some embodiments, the terminal device 150 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing engine 120 via, for example, a bus, for further processing. Other types of the input device may include a cursor control device, such as a mouse, a trackball, or cursor direction keys, etc. The output device may include a display, a speaker, a printer, or the like, or any combination thereof. In some embodiments, the terminal device 150 may be part of the processing engine 120.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the storage device 140 may be a data storage including cloud computing platforms, such as public cloud, private cloud, community, hybrid clouds, etc. In some embodiments, the processing engine 120 may be integrated into the therapeutic apparatus 110. However, those variations and modifications do not depart the scope of the present disclosure.

Figure 2:
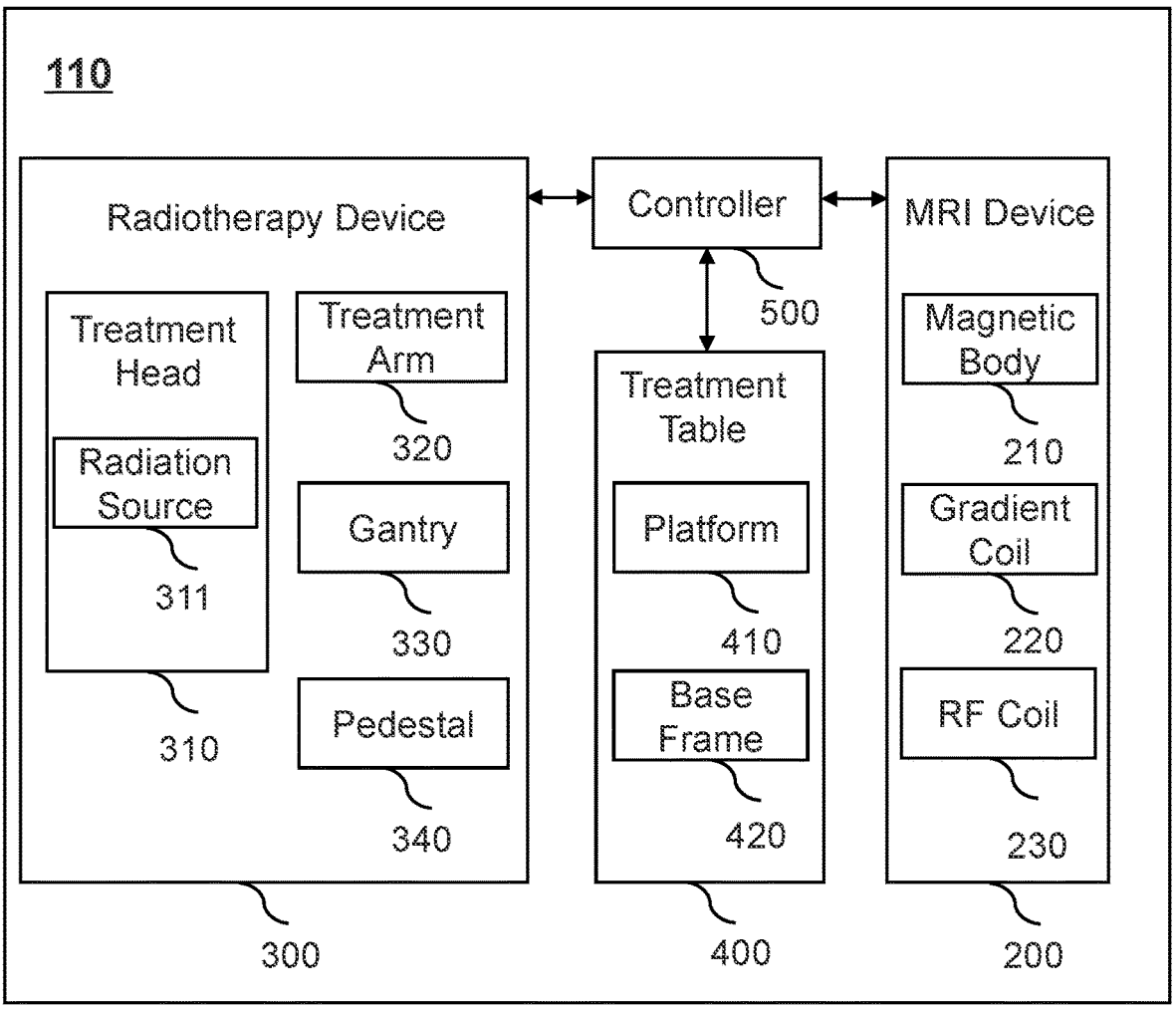
FIG. 2 is a block diagram illustrating an exemplary therapeutic apparatus according to some embodiments of the present disclosure.

FIG. 2 is a block diagram illustrating an exemplary therapeutic apparatus 110 according to some embodiments of the present disclosure. The therapeutic apparatus 110 may include an MRI device 200, a radiotherapy device 300, a treatment table 400, and a controller 500. It is understood that the MRI device 200 is referred to herein for illustration purposes only, and not intended to limit the scope of the present disclosure. The description provided herein may be applied in other devices or systems including, for example, a positron emission tomography-magnetic resonance imaging (PET-MRI) device, a positron emission tomography-radiotherapy (PET-RT) system, etc.

The MRI device 200 may include a magnetic body 210, one or more gradient coils 220, and one or more radiofrequency (RF) coils 230. The magnetic body 210 may generate a static magnetic field BO during an MRI process. The magnetic body 210 may be of various types including, for example, a permanent magnet, a superconducting electromagnet, a resistive electromagnet, etc. The superconducting electromagnet may include niobium, vanadium, technetium alloy, etc.

The gradient coil 220 may generate magnetic field gradients to the main magnetic field BO in the X, Y, and/or Z directions (or axes). In some embodiments, the gradient coil may include an X-direction coil (or axis), a Y-direction coil (or axis), a Z-direction coil (or axis), etc. For example, the Z-direction coil may be designed based on circular (Maxwell) coil, while the X-direction coil and the Y-direction coil may be designed on the basis of the saddle (Golay) coil configuration. As used herein, the X direction may also be referred to as the readout (RO) direction (or a frequency encoding direction), the Y direction may be also referred to the phase encoding (PE) direction, the Z direction may also be referred to the slice selecting encoding (SPE) direction. In the present disclosure, the readout direction and the frequency encoding direction may be used interchangeably. The gradient magnetic fields may include a slice selecting encoding (SPE) gradient field corresponding to Z-direction, a phase encoding (PE) gradient field corresponding to Y-direction, a readout (RO) gradient field corresponding to X-direction, etc. The gradient magnetic fields in different directions may be used to encode the spatial information of MR signals. In some embodiments, the gradient magnetic fields may also be used to perform at least one function of flow encoding, flow compensation, flow dephasing, or the like, or any combination thereof.

The RF coil 230 may emit RF pulse signals to and/or receive MR signals from a subject (e.g., a human body) being examined. In some embodiments, the RF coil may include an RF transmitting coil and an RF receiving coil. The RF transmitting coil may emit RF pulse signals that may excite the nucleus in the human body to resonate at the Larmor frequency. The RF receiving coil may receive MR signals emitted from the human body. In some embodiments, the RF transmitting coil and RF receiving coil may be integrated into one single coil, for example, a transmitting/receiving coil. The RF coil 230 may be of various types including, for example, a OD orthogonal coil, a phase-array coil, a specific element spectrum coil, etc. In some embodiments, the RF coil 230 may be different according to different parts of a body being examined, for example, a head coil, a knee joint coil, a cervical vertebra coil, a thoracic vertebra coil, a temporomandibular joint (TMJ) coil, etc. In some embodiments, according to function and size, the RF coil 230 may include a volume coil, a local coil, a birdcage coil, a transverse electromagnetic coil, a surface coil, a saddle coil, or the like, or any combination thereof. As another example, the local coil may include a solenoid coil, a saddle coil, a flexible coil, etc. In some embodiments, the MRI device 200 may be a permanent magnet MR scanner, a superconducting electromagnet MR scanner, or a resistive electromagnet MR scanner, etc., according to types of the magnetic body. In some embodiments, the MRI device 200 may be a high-field MR scanner, a mid-field MR scanner, and a low-field MR scanner, etc., according to the intensity of the magnetic field.

It should be noted that the above description is merely provided for the purposes of illustration, and not intended to limit the scope of the present disclosure. For persons having ordinary skills in the art, multiple variations or modification may be made under the teaching of the present disclosure. For example, the MRI device 200 may further include a shield coil, a shim coil, a cooling device, a liquid helium Dewar vessel, or the like, or any combination thereof. However, those variations and modifications do not depart from the scope of the present disclosure.

The radiotherapy device 300 may include a treatment head 310, a treatment arm 320, a gantry 330, and a pedestal 340. The treatment head 310 may be configured to emit a radiation beam. For example, the treatment head 310 may include a radiation source 311 to emit the radiation beam. The radiation beam may be an X-ray beam, an electron beam, a gamma ray source, a proton ray source, etc. The treatment head 310 may be used to direct a radiation beam generated by the radiation source 311 into a treatment region. The treatment head 310 may be installed on the gantry 330 by the treatment arm 320. The gantry 330 may be supported by the pedestal 340. The treatment arm 320 may be any length desired. In some embodiments, the treatment arm 320 may have a length sufficient to position the treatment head 310. In some embodiments, the treatment arm 320 may have a length sufficient to accelerate particles, such as electrons. In some embodiments, the treatment head 310 may include an electron beam generator.

It should be noted that the above description is merely provided for the purposes of illustration, and not intended to limit the scope of the present disclosure. For persons having ordinary skills in the art, multiple variations or modification may be made under the teaching of the present disclosure. For example, the radiotherapy device 300 may further include a linear accelerator (LINAC) configured to accelerate electrons, ions, or protons, a dose detecting device, a temperature controlling device (e.g., a cooling device), a multiple layer collimator, or the like, or any combination thereof. However, those variations and modifications do not depart from the scope of the present disclosure.

The treatment table 400 may include a platform 410 for supporting a patient and a base frame 420. In some embodiments, the treatment table 400 may further include a patient positioning system for adjusting the position of a patient so that a treatment region (e.g., a tumor) in the patient may receive treatment rays from the radiotherapy device 300.

The controller 500 may be configured to control the radiotherapy device 300, the treatment table 400, and/or the MRI device 200. In some embodiments, the terminal device 150 may send an instruction to the processing engine 120 for processing. The controller 500 may obtain the instruction processed by the processing engine 120 to control the radiotherapy device 300, the treatment table 400, and/or the MRI device 200. In some embodiments, the controller 500 may control an angle of the gantry 330 by rotating the gantry 330. In some embodiments, the controller may control the MRI device 200 to image a treatment region. For example, the controller 500 may perform specific functions related to a scanning of a part of an imaged subject. In some embodiments, the controller 500 may control a cooling system built in the magnetic body 210 of the MRI device 200, and the magnetic body 210 may be maintained in a super-low temperature environment generated by the cooling system. In some embodiments, the controller 500 may adjust a height or a position of the platform 410 by a positioning system built in or operably connected to the treatment table 400 to properly position a patient so that a treatment region (e.g., a cancerous tumor or lesion) in the patient may receive treatment rays from the radiotherapy device 300. In some embodiments, the controller 500 may drive the platform 410 of the treatment table 400 to move along an axis of the magnetic body 210. In some embodiments, the controller 500 may cause the platform 410 of the treatment table 400 to move two-dimensionally or three-dimensionally. The movement may include, for example, translation, rotation, or the like, or a combination thereof. In some embodiments, the controller 500 may cause the platform 410 of the treatment table to be positioned such that the tumor is positioned on the axis 370 of the radiotherapy device 300. In some embodiments, the controller 500 may move the platform 410 of the treatment table 400 according to a real time MR image obtained shortly before or during a treatment as described elsewhere in the present disclosure. In some embodiments, the controller 500 may drive a treatment head to rotate around the MRI device 200. In some embodiments, the controller 500 may further cause the treatment head to arrive at a suitable position to emit radiation toward a treatment region.

Figure 3:
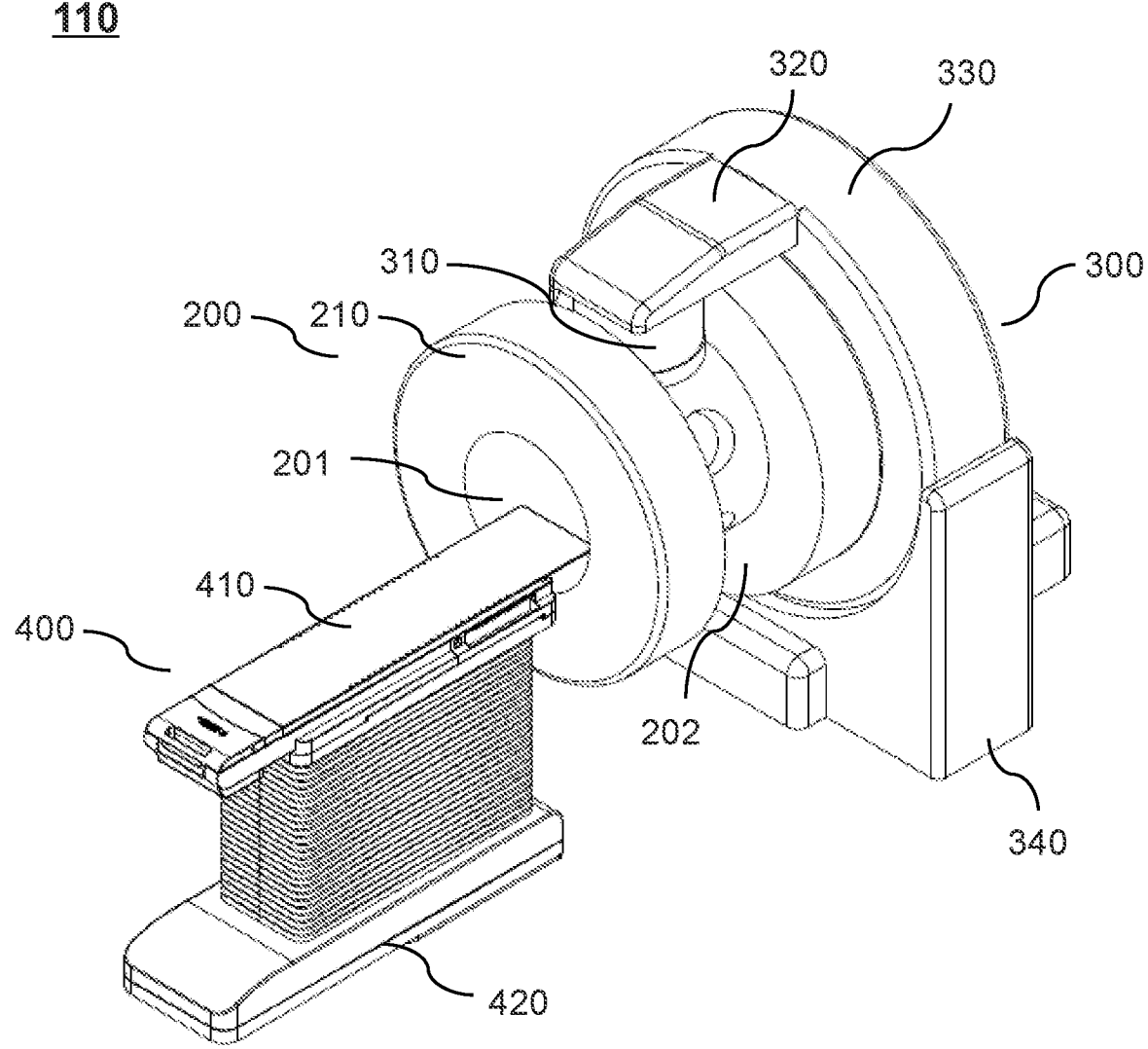
FIG. 3 illustrates an exemplary therapeutic apparatus according to some embodiments of the present disclosure.

FIG. 3 illustrates an exemplary therapeutic apparatus 110 according to some embodiments of the present disclosure. As illustrated in FIG. 3, the therapeutic apparatus 110 may include an MRI device 200, a radiotherapy device 300, and a treatment table 400. The MRI device 200 may include a bore 201, a magnetic body 210, and a recess 202. The bore 201 may accommodate a patient. The MRI device 200 may be configured to acquire image data from an imaging region. For example, the image data may relate to the treatment region associated with a tumor. The treatment table 400 may include a platform 410 and a base frame 420. In some embodiments, the platform 410 may move along the horizontal direction and enter into the bore 201 of the MRI device 200. In some embodiments, the platform 410 may move two-dimensionally or three-dimensionally. In some embodiments, the platform 410 may move according to the position change of the tumor estimated by, for example, a real time MR image obtained during a treatment. The radiotherapy device 300 may include a treatment head 310, a treatment arm 320, a gantry 330, and a pedestal 340. In some embodiments, a treatment region (e.g., a tumor) may be determined according to the image data acquired from the MRI device 200. Then a radiation beam may be generated by the radiation source 311 (as described in FIG. 2) according to the treatment region. The therapeutic apparatus 110 may provide the radiation beam on the treatment region simultaneously with or subsequent to the imaging. For example, the dose of the radiation beam and/or the position of the treatment region may be determined in real time with the assistance of the MRI device 200 as described in connection with FIG. 1. More detailed description related to the therapeutic apparatus 110 may be found elsewhere in the present disclosure. See, for example, FIG. 4, FIG. 5, FIG. 6, and FIG. 7.

Figure 4:
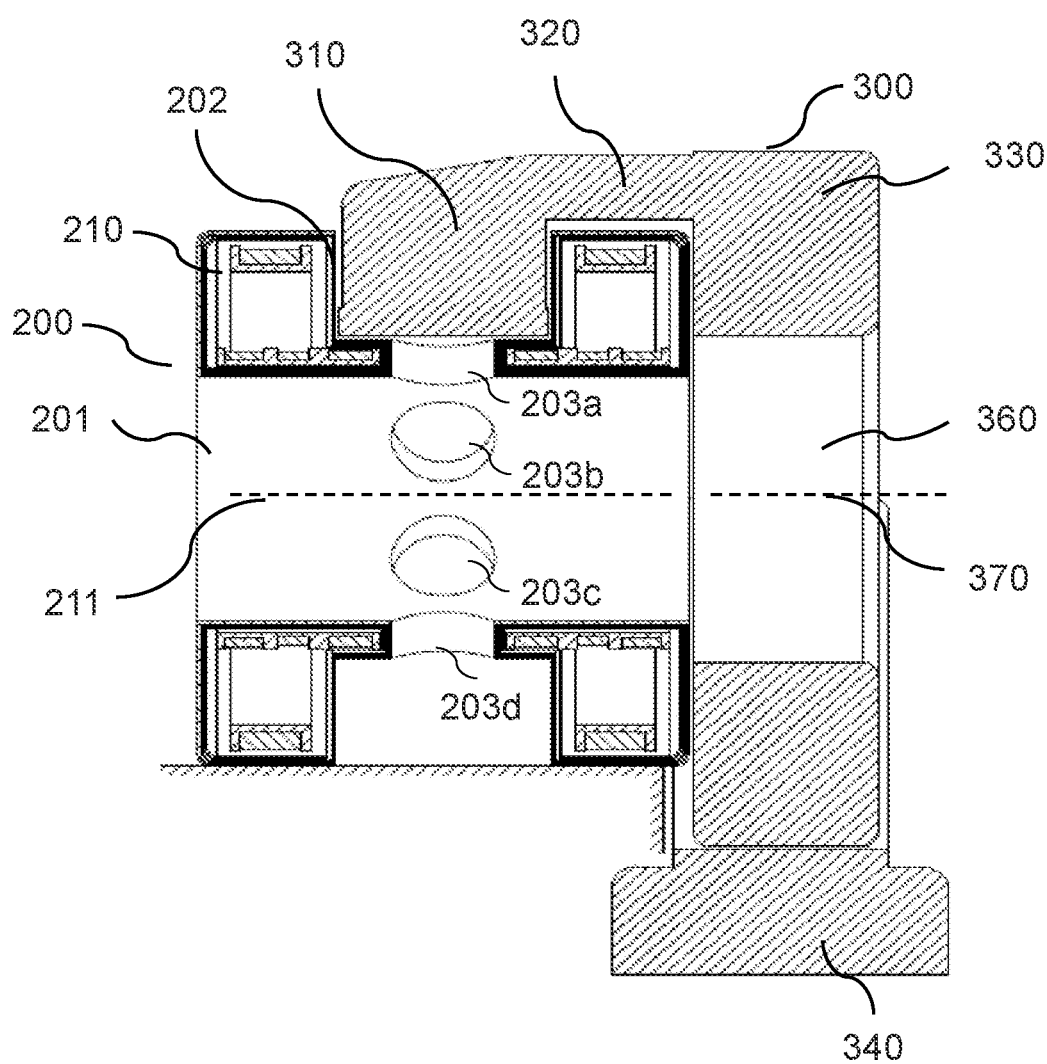
FIG. 4 shows a cross-sectional view of an exemplary therapeutic apparatus according to some embodiments of the present disclosure.

FIG. 4 shows a cross-sectional view of an exemplary therapeutic apparatus 110 according to some embodiments of the present disclosure. As shown in FIG. 4, the therapeutic apparatus 110 may include an MRI device 200 and a radiotherapy device 300. The MRI device 200 may include a magnetic body 210 and a bore 201. The bore 201 may have a first axis 211 (marked as the dotted line in FIG. 4). The radiotherapy device 300 may include a treatment head 310, a treatment arm 320, a gantry 330, and a pedestal 340, and a bore 360. The bore 360 may have a second axis 370 (marked as the dotted line in FIG. 4) in the gantry 330. In some embodiments, the first axis 211 may coincide with or approximately coincide with the second axis 370.

In some embodiments, the treatment head 310 and part of the treatment arm 320 may be set around the magnetic body 210. In some embodiments, the magnetic body 210 may include a recess 202 on its outer wall. In some embodiments, the recess 202 may be disposed around the entire circumference of the magnetic body 210. For example, the recess 202 may have the shape of a circle surrounding the magnetic body 210. In some embodiments, the recess 202 may be disposed around part of the circumference of the magnetic body 210. For example, the recess 202 may have the shape of one or more arcs surrounding the magnetic body 210.

In some embodiments, the recess 202 may accommodate at least a portion of the treatment head 310. This arrangement may reduce a distance between the treatment head 310 and the axis 211 of the bore 201. In some embodiments, the reduction in the distance between the treatment head 310 and the axis 211 of the bore 201 may bring about an increase of the radiation dose that may reach the treatment region (e.g., a tumor) and/or an enhancement in the therapeutic efficiency. In some embodiments, the width of the recess 202 may be no less than the width of the treatment head 310. In some embodiments, by controlling the gantry 330 by the controller 500, the treatment head 310 may rotate at least partially within the recess 202 of the magnetic body 210. For example, during treatment, by rotating the gantry 330, the radiation beam from the treatment head 310 may be directed toward a treatment region at any angle (e.g., 0 degree, 15 degrees, 30 degrees, 60 degrees, 120 degrees).

In some embodiments, the recess 202 may include a first opening 203a, a second opening 203b, a third opening 203c, and a fourth opening 203d. In some embodiments, the openings may be distributed uniformly. For example, the angle between the axes of two adjacent openings may be the same value, for example, 180 degrees, 120 degrees, 90 degrees, 72 degrees, 60 degrees, 45 degrees, 30 degrees, etc. Merely by way of example, the angle between the axes of two adjacent openings among the openings 203a through 203d may be 90 degrees. In some embodiments, the openings may be distributed at the bottom of the recess 202 randomly or according to a rule. For example, more openings may be located on the upper half of the magnetic body 210 than on the lower half part of the magnetic body 210, or vice versa. In some embodiments, an opening of the recess 202 may have the shape of, for example, a rectangle, a rounded rectangle, a rhombus, a circle, a triangle, a trapezoid, an ellipse, an irregular shape, a polygon, a rounded polygon, or the like, or any combination thereof. For example, as exemplified in FIG. 4, each of the openings 203a, 203b, 203c, and 203d may have the shape of a circle. The openings 203a, 203b, 203c, and 203d may be of a same size or different sizes. As another example, the first opening 203a may have a shape of a rounded rectangle. Then the first opening 203a may correspond to an arc of the circumference of the recess 202. The arc may range from 0 to $2\pi$ radians. Merely by way of example, the arc may range from $1/10\pi$ radians to $3/2\pi$ radians, for example, $1/6\pi$ radians, $1/3\pi$ radians, $1/2\pi$ radians, $1\pi$ radians, $3/2\pi$ radians, etc. An axis of an opening (e.g., any one of the openings 203a through 203d) may refer to a centerline of the opening pointing from the outside of the bore 201 to the axis 211 of the bore 201 (or vice versa). As used herein, a centerline of the opening may refer to a line that passes the geometric center, the mass center, etc., of the opening and perpendicular to the plane where the opening is located. In some embodiments, the openings 203a, 203b, 203c, or 203d may also be filled up by a material that is at least partially radiation transparent. Merely by way of example, the material may slightly absorb or hinder a radiation beam generated by the radiation source 311. The material may be, e.g., epoxy resin or a light metal.

In some embodiments, the treatment head 310 may rotate by moving along the recess 202 and arrive at or pass through a position corresponding to any one of the openings 203a through 203d. The treatment head 310 may move or generate the radiation beam according to parameters determined by an original treatment plan or an adjusted treatment plan. The original treatment plan Exemplary parameters may be associated with the radiation beam, the treatment head 310, or the platform 410.

For example, parameters of the radiation beam may include an irradiating intensity, an irradiating angle, an irradiating distance, an irradiating area, an irradiating time, an intensity distribution, or the like, or any combination thereof. A parameter of the radiation beam may be adjusted by adjusting the treatment head 310, the platform 410, or the like, or a combination thereof. Parameters of the treatment head 310 may include a position, a rotating angle, a rotating speed, a rotating direction, the configuration of the treatment head 310, or the like, or any combination thereof. For instance, the treatment head 310 may include a multi-leaf collimator (MLC), The MLC may be adjusted to adjust the irradiating area, etc., of the treatment beam. In some embodiments, the original treatment plan or the adjusted treatment plan may also take into consideration energy loss of the radiation beam due to, e.g., the magnetic body 210 located in the pathway of the radiation beam that may absorb at least a portion of the radiation beam. For example, the irradiating intensity of the radiation beam may be set larger than that in the situation in which there is no energy loss due to, e.g., the absorption by the magnetic body 210 accordingly to compensate the energy loss such that the radiation beam of a specific intensity may impinge on a treatment region (e.g., a tumor).

Parameters of the platform 410 may include a position, a height, a rotating angle, or the like, or any combination thereof. In some embodiments, parameters of the treatment plan may be dynamically adjusted based on a position of a treatment region (e.g., a tumor) determined based on an MR image acquired shortly before or during a treatment. For example, such an MR image may be acquired less than 1 day, or half a day, or 6 hours, or 3 hours, or 1 hour, or 45 minutes, or 30 minutes, or 20 minutes, or 15 minutes, or 10 minutes, or 5 minutes, etc., before the treatment head 310 starts emitting a radiation beam for treatment based on an original treatment plan or an adjusted treatment plan (e.g., an original treatment adjusted based on the acquired MR image). For example, the positon of the treatment head 310 or the platform 410 may be adjusted so as to position the tumor on the axis 370 of the radiotherapy device 300. The original treatment plan may be determined before the treatment commences. For instance, the original treatment plan may be determined at least one day, or three days, or a week, or two weeks, or a month, etc., before the treatment commences. The treatment region may change between when the treatment plan is determined and when the treatment is carried out.

In some embodiments, the treatment head 310 may stop rotating intermittently. For instance, the treatment head 310 may rotate to a desired position corresponding to an opening (e.g., any one of the openings 203a through 203d), pause there, and emit a radiation beam, and then resume to rotate. In some embodiments, the treatment head 310 may rotate continuously, and emit a radiation beam continuously or intermittently.

In some embodiments, the treatment head 310 may be moved to and matched to any one of the openings 203a, 203b, 203c, and 203d to arrive at a suitable position, for example, the axis of the treatment head 310 may coincide with the axis of an opening. Then the treatment head 310 may emit a radiation beam. In some embodiments, the treatment head 310 may emit the radiation beam 360 when it is positioned at a position not corresponding to an opening (e.g., the first opening 203a). For instance, the treatment head 310 may emit the radiation beam when it is positioned at a position not corresponding to an opening (e.g., the first opening 203a). Merely by way of example, the treatment head 310 may continuously emit the radiation beam while rotating. If the treatment head 310 emits the radiation beam when it is positioned at a position not corresponding to an opening (e.g., the first opening 203a), there may be a portion of the system 100 (e.g., the magnetic body 210 of the MR device 200) located in the pathway of the radiation beam 360 toward the treatment region, and at least a portion of the emitted radiation beam may be absorbed by, e.g., the magnetic body 210.

It should be noted that the above description of the therapeutic apparatus 110 is merely provided for the purposes of illustration, and not intended to limit the scope of the present disclosure. For persons having ordinary skills in the art, multiple variations and modifications may be made under the teachings of the present disclosure. For example, the assembly and/or function of the therapeutic apparatus 110 may vary or change according to a specific implementation scenario. In some embodiments, the magnetic body 210 of the MRI device 200 may also rotate relative to the treatment head 310. For example, the radiotherapy device 300 and the MRI device 200 may synchronously or asynchronously rotate around a same axis (e.g., the axis 211 or the axis 370). However, those variations and modifications do not depart from the scope of the present disclosure.

Figure 5:
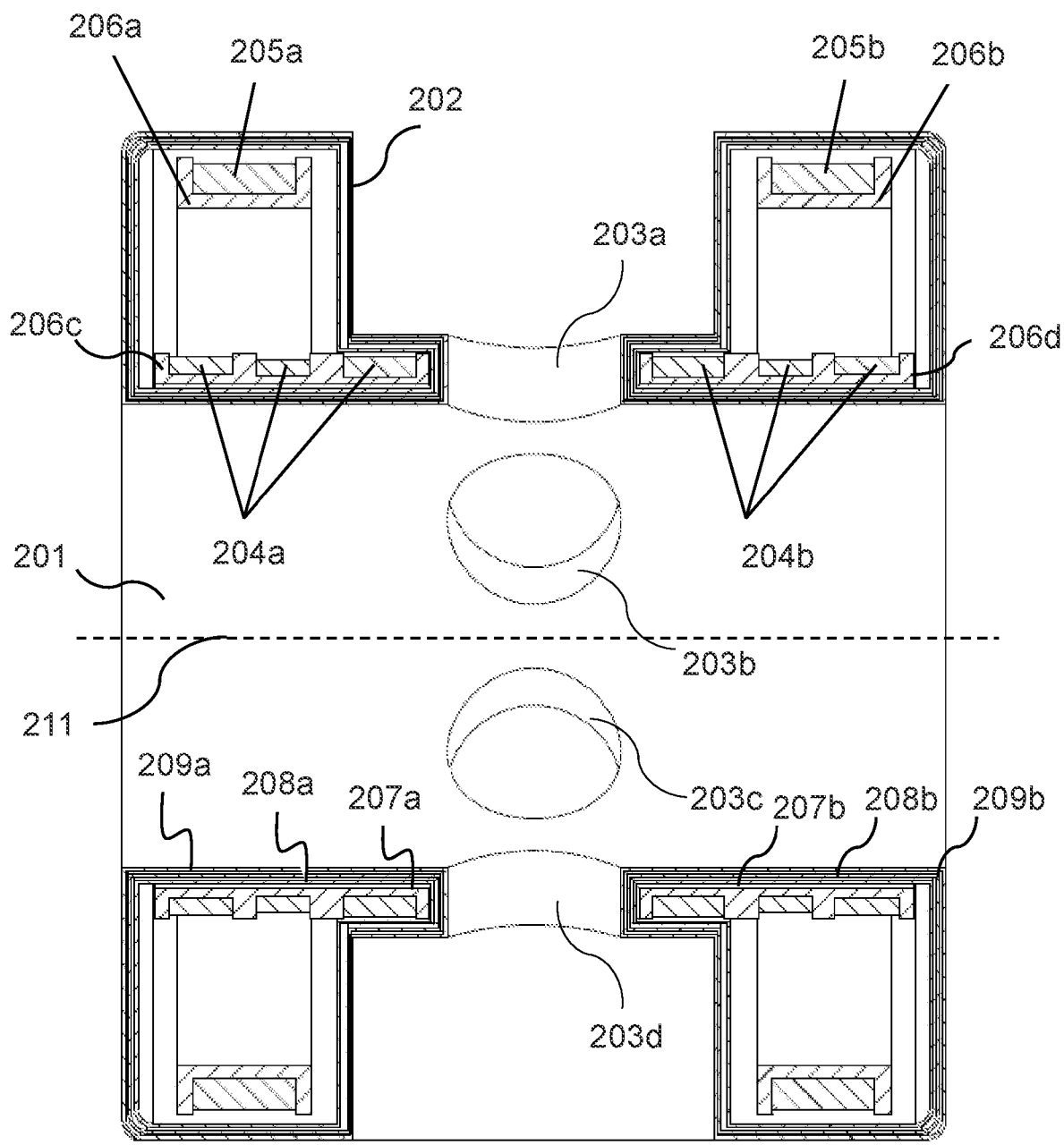
FIG. 5 shows a cross-sectional view of an exemplary magnetic body according to some embodiments of the present disclosure.

FIG. 5 shows a cross-sectional view of an exemplary magnetic body 210 according to some embodiments of the present disclosure. The magnetic body 210 may include one or more main coils (e.g., a first main coil 204a, and a second main coil 204b) configured to generate a main magnetic field, one or more openings (e.g., a first opening 203a, a second opening 203b, a third opening 203c, and a fourth opening 203d) in the recess 202, one or more shield coils (e.g., a first shield coil 205a and a second shield coil 205b), one or more bobbins (e.g., a first bobbin 206a and a second bobbin 206b, a third bobbin 206c, and a fourth bobbin 206d), one or more cooling layers (e.g., a first cooling layer 207a and a second cooling layer 207b), one or more thermal insulation layers (e.g., a first thermal insulation layer 208a and a second thermal insulation layer 208b), and one or more vacuum layers (e.g., a first vacuum layer 209a and a second vacuum layer 209b). In some embodiments, the one or more main coils (e.g., a first main coil 204a, and a second main coil 204b) may be electrically connected to each other through, e.g., an electrically conductive wire.

In some embodiments, the main coils 204a and 204b and/or the shield coils 205a and 205b may be superconductive at least under some condition (e.g., when the coils are maintained at a suitable temperature). The direction of the current in the shield coils 205a and 205b may be opposite to the direction of the current in the main coils 204a and 204b. An inner diameter of the shield coils 205a and 205b may be greater than an external diameter of the main coils 204a and 204b to shield an escaped magnetic field generated by the main coils 204a and 204b. The escaped magnetic field may attract a ferromagnetic substance resulting in damage to or interference with the operation of some medical devices including, for example, the MRI device 200, a PET-RT device, etc. In some embodiments, the main coils 204a and 204b may be integrated into one main coil. In some embodiments, the left part and the right part of the magnetic body 210 may share the same cooling system. For example, one cooling system having one inlet for fresh cooling medium and one exit for the used cooling medium may cool the connected left part and the right part of the magnetic body 210. In some embodiments, the left part and the right part of the magnetic body 210 may be cooled by separate cooling devices.

In some embodiments, the depth dx1 of the recess 202 of the opening 203a and the depth dx2 of the opening (e.g., the first opening 203a) may be determined according to the size of the magnetic body 210, and a desired irradiating distance. In some embodiments, dx1 and dx2 may be determined by formulas below:

$$dx1 = d1/2 - d3, \quad (1)$$

$$dx2 = (d1-d2)/2 - dx1, \quad (2)$$

where d1 refers to the external diameter of the magnetic body 210, d2 refers to the inner diameter of the magnetic 210, and d3 refers to a distance between an end face of the treatment head 310 and the axis 211. For example, if the external diameter d1 of the magnetic body 210 is 2 meters, the inner diameter d2 of the magnetic body 210 may be, for example, 60~70 centimeters, and the irradiating distance requirement (e.g., the distance d3 between the end face of the treatment head 310 and the axis 211) may be, for example, 40~50 centimeters. According to formulas (1) and (2), dx1 may be about 50~60 centimeters, dx2 may be about 5~20 centimeters.

In some embodiments, the width w1 of the recess 202 may be determined according to the size of the treatment head 310. For example, the value of the width w1 may be larger than the width of the treatment head 310. For instance, w1 may be at least 102%, or 105%, or 108%, or 110%, or 115%, or 120%, etc., of the width of the treatment head 310. In some embodiments, the width w2 of the opening (e.g., the first opening 203a) may be of a suitable value, for example, a value not greater than w1. For instance, w1 may be at least 102%, or 105%, or 108%, or 110%, or 115%, or 120%, etc., of w2.

In some embodiments, the cooling layers 207 (e.g., 207a and 207b as illustrated in FIG. 5) may be configured to achieve a desired uniformity and/or a desired stability of the temperature of the main coils 204a and 204b. For instance, a desired uniformity of the temperature of the main coils 204a and 204b may be that the difference between the highest temperature and the lowest temperature within the main coils 204a and 204b at a time point is below 20° C., or 15° C., or 10° C., or 8° C., or 5° C., or 2° C., or 1° C., etc. As used herein, a desired stability of the temperature of the main coils 204a and 204b may be that the rate or the value of the temperature change (e.g., compared to a standard temperature that is suitable for the proper operation of the main coils) in the main cons 204a and 204b during one operation is below a respective threshold. For instance, a desired stability of the temperature of the main coils 204a and 204b may be that the rate of the temperature change in the main coils 204a and 204b is below 20° C./minute, or 15° C./minute, or 10° C./minute, or 8° C./minute, or 5° C./minute, or 2° C./minute, or 1° C./minute, etc. As another example, a desired stability of the temperature of the main coils 204a and 204b may be that the value of the temperature change (e.g., a deviation from a standard temperature) in any portion of the main coils during one operation is below 20° C., or 15° C., or 10° C., or 8° C., or 5° C., or 2° C., or 1° C., etc. As a further example, a desired stability of the temperature of the main coils 204a and 204b may be that the rate and the value of the temperature change (e.g., compared to a standard temperature that is suitable for the proper operation of the main coils) in the main coils is below a respective threshold.

In some embodiments, the cooling layers 207a and 207b may include one or more cooling media capable of generating or maintaining a super-low temperature environment. Exemplary cooling media may include liquid nitrogen, etc. The thermal insulation layers 208a and 208b may be mounted outside of the cooling layers 207a and 207b, respectively. The vacuum layers 209a and 209b may be mounted outside of the thermal insulation layers 208a and 208b, respectively. The main coils 204a and 204b may be wound around the bore 201 of the MRI device 200. In some embodiments, the main coils 204a and 204b may be wound around the bobbins 205a and 205b, respectively. When current passes through the main coils 204a and 204b, a magnetic field may be generated in the bore 201 and the direction of the magnetic field may be parallel to the axis 211. In some embodiments, the main cons 204a and 204b may be electrically connected by, for example, an electrically conductive wire. The strength of the magnetic field generated by the main coils 204a and 204b may relate to the number of turns of the main coils 204a and 204b. The shield coils 206a and 206b may be wound around the bobbins 206a and 206b, respectively.

In some embodiments, the first cooling layer 207a and the second cooling layer 207b may be different parts in fluid communication of an integrated cooling layer. The first thermal insulation layer 208a and the second thermal insulation layer 208b may be different parts of an integrated thermal insulation layer. The first vacuum layer 209a and the second vacuum layer 209b may be different parts in fluid communication of an integrated vacuum layer. The first vacuum layer 209a and the second vacuum layer 209b forming parts in fluid communication may indicate that a fluid including, for example, a gas, in the integrated vacuum layer may fill the first vacuum layer 209a and the second vacuum layer 209b.

It should be noted that the above description is provided for the purposes of illustration, and not intended to limit the scope of the present disclosure. Apparently, for persons having ordinary skills in the art, numerous variations and modifications may be conducted under the teaching of the present disclosure. However, those variations and modifications do not depart the protection scope of the present disclosure. For example, the size, the number, the shape, the distribution of the recess 202 are not limited to those as exemplified in FIG. 5 and the description thereof. Similar modifications should fall within the scope of the present disclosure.

Figure 6:
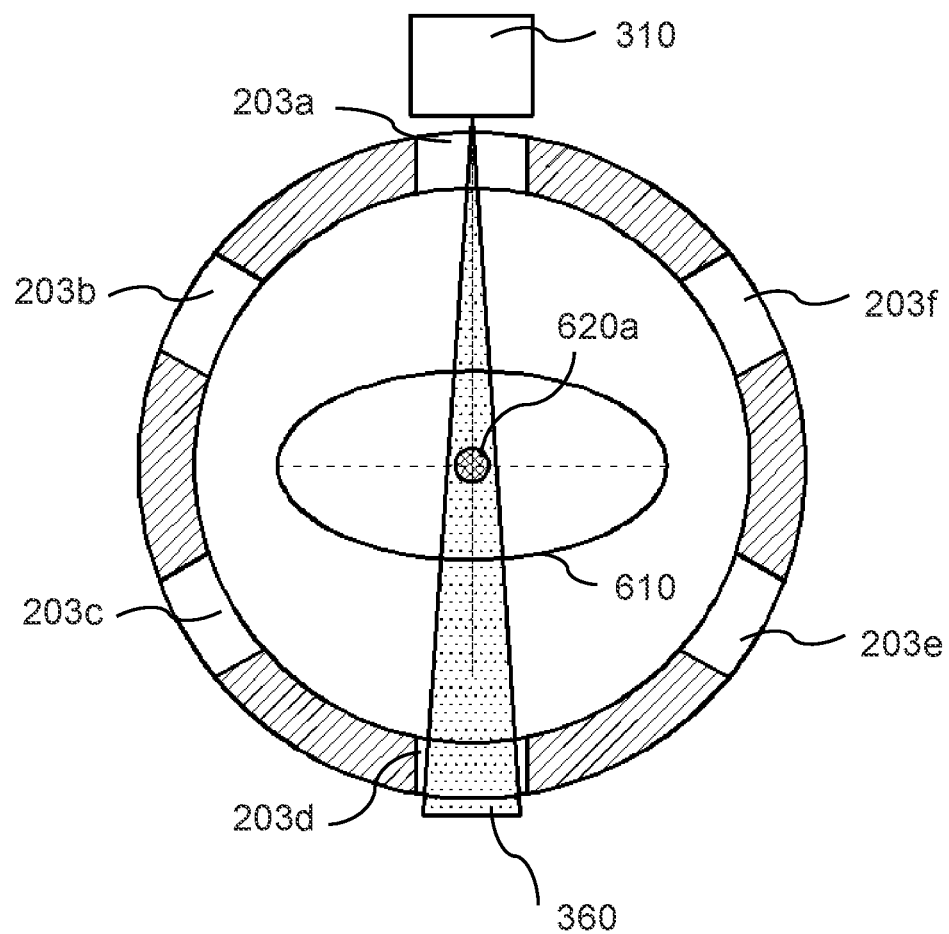
FIG. 6 shows a cross-sectional view of some components of an exemplary therapeutic apparatus according to some embodiments of the present disclosure.

FIG. 6 shows a cross-sectional view of some components of an exemplary therapeutic apparatus 110 according to some embodiments of the present disclosure. The recess 202 may include a first opening 203a, a second opening 203b, a third opening 203c, a fourth opening 203d, a fifth opening 203e, and a sixth opening 203f. As shown in Fla 6, the six openings 203a-203f may be distributed uniformly. Each opening has a corresponding opening at the opposite position on the recess 202. As used herein, two openings may be regarded as opposite or opposing if the two openings are 180 degrees apart, or if a line linking the two openings passes the axis 211 of the bore 201. Two opposite or opposing openings may also be described as being located at opposite directions or positions. Merely by way of example, the first opening 203a has a corresponding fourth opening 203d at the opposite direction. The arc of an opening (e.g., any one of the six openings 203a-203f) may range from 0 to $2\pi$ radians including, for example, $1/12\pi$ radians, $1/9\pi$ radians, $1/6\pi$ radians, etc. In some embodiments, the openings may be distributed on the recess 202 randomly or according to a rule. For example, more openings may be located on the upper half of the magnetic body 210 than on the lower half of the magnetic body 210, or vice versa. In some embodiments, the openings of the recess 202 may be of the same size or different sizes.

The region labeled 360 may be a radiation beam generated by a radiation source 311 in the treatment head 310. A patient 610 having a treatment region 620a (e.g., a tumor) may be positioned in the center (or the axis 211) of the bore 201 and the treatment region 620a may be positioned at the isocenter of the radiotherapy device 300. The treatment head 310 located at least partially within the recess 202 may rotate and radiate toward the treatment region 620a Merely by way of example, the treatment head 310 has six positions for emitting radiation, for example, the treatment head 310 may be in a position corresponding to the first opening 203a (as shown in FIG. 6). The radiation beam 360 may travel along a path that traverses the treatment region 620a In some embodiments, the treatment head 310 may also be in a position corresponding to the fourth opening 203d.

In some embodiments, the treatment head 310 may rotate and arrive at a position corresponding to an opening (e.g., the first opening 203a), and emit the radiation beam 360 only when it is positioned at such a position corresponding to an opening (e.g., the first opening 203a). The radiation beam 360 from the treatment head 310 may reach the treatment region without substantial absorption of the radiation beam 360 by the magnetic body 210.

In some embodiments, the treatment head 310 may also rotate and may emit the radiation beam 360 when it is positioned at a position not corresponding to an opening (e.g., the first opening 203a). For instance, the treatment head 310 may emit the radiation beam 360 when it is positioned at a position not corresponding to an opening (e.g., the first opening 203a). Merely by way of example, the treatment head 310 may continuously emit the radiation beam 360 while rotating. If the treatment head 310 emits the radiation beam 360 when it is positioned at a position not corresponding to an opening (e.g., the first opening 203a), at least a portion of the emitted radiation beam 360 may be absorbed by, e.g., the magnetic body 210.

As shown in FIG. 6, the radiation source 311 may be closer to the treatment region 620a, because there is the recess 202 in the outer wall of the magnetic body 210 for accommodating at least part of the treatment head 310. The first opening 203a at the bottom of the recess 202 may allow radiation beams emitted by the treatment head 310 to pass through to reach the treatment region 620a without substantial attenuation. In some embodiments, the reduction in the distance between the treatment head 310 and the axis 211 of the bore 201 may bring about an increase of the radiation dose reaching the treatment region (e.g., a tumor) and/or an enhancement in the therapeutic efficiency.

Figure 7:
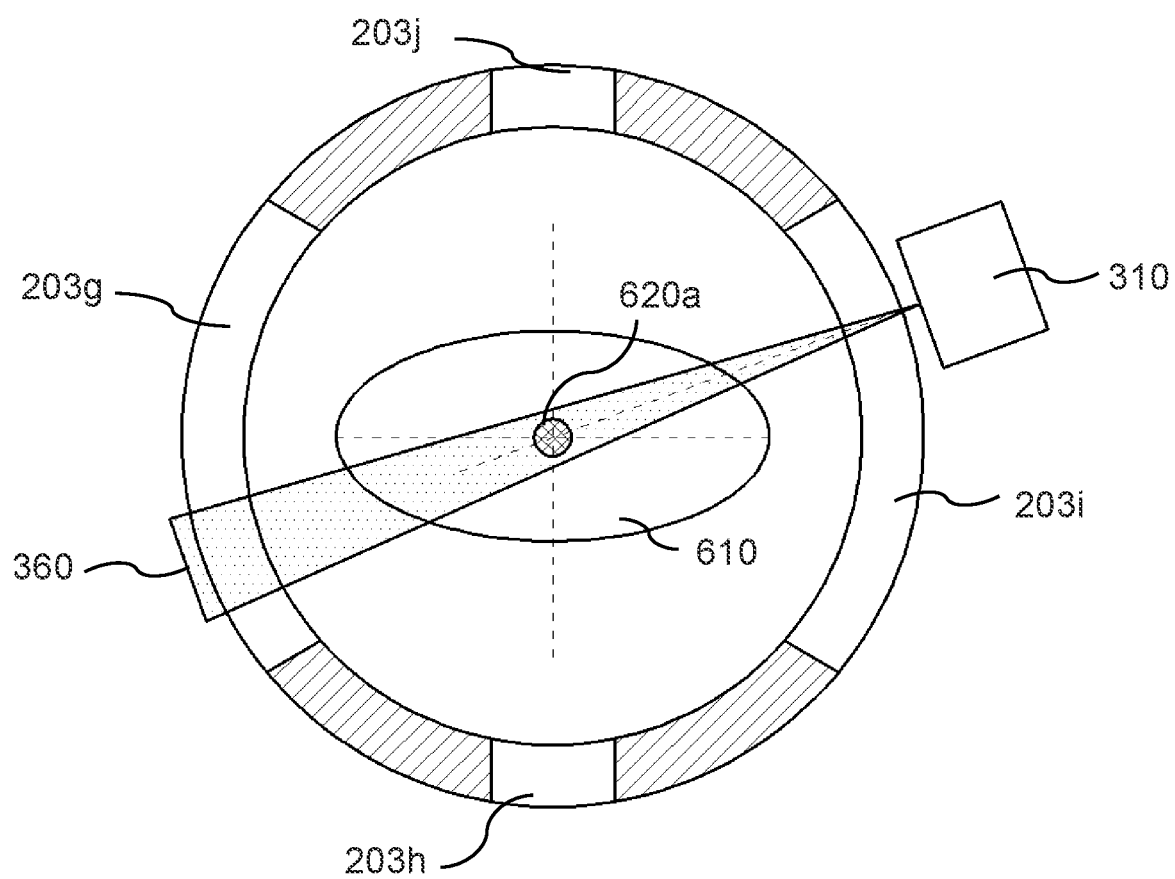
FIG. 7 shows a cross-sectional view of some components of an exemplary therapeutic apparatus according to some embodiments of the present disclosure.

FIG. 7 shows a cross-sectional view of some components of an exemplary therapeutic apparatus 110 according to some embodiments of the present disclosure. The recess 202 may include a seventh opening 203g, an eighth opening 203h, a ninth opening 203i, and a tenth opening 203j. As shown in FIG. 7, the seventh opening 203g may be at the opposite position of the ninth opening 203i, and the eighth opening 203h may be at the opposite position of the tenth opening 203j. In some embodiments, the seventh opening 203g and/or the ninth opening 203i may correspond to a lager arc of the circumference of the recess 202 compared with the eighth opening 203h and/or the tenth opening 203j. The arc of the seventh opening 203g and/or the arc of the ninth opening 203i may range from $1/4\pi$ to $2\pi$ radians including, for example, $1/3\pi$ radians, $1/2\pi$ radians, $1\pi$ radians, $3/2\pi$ radians, etc.

In some embodiments, at least one of the seventh opening 203g, the eighth opening 203h, the ninth opening 203i, or the tenth opening 203j may be optional. For example, the recess 202 may merely include the seventh opening 203g and/or the ninth opening 203i, or merely include the seventh opening 203g. In some embodiments, the positions of the seventh opening 203g, the eighth opening 203h, the ninth opening 203i, or the tenth opening 203j may be changed. Merely by way of example, the seventh opening 203g may be moved to the position of the tenth opening 203j.

Figure 8:
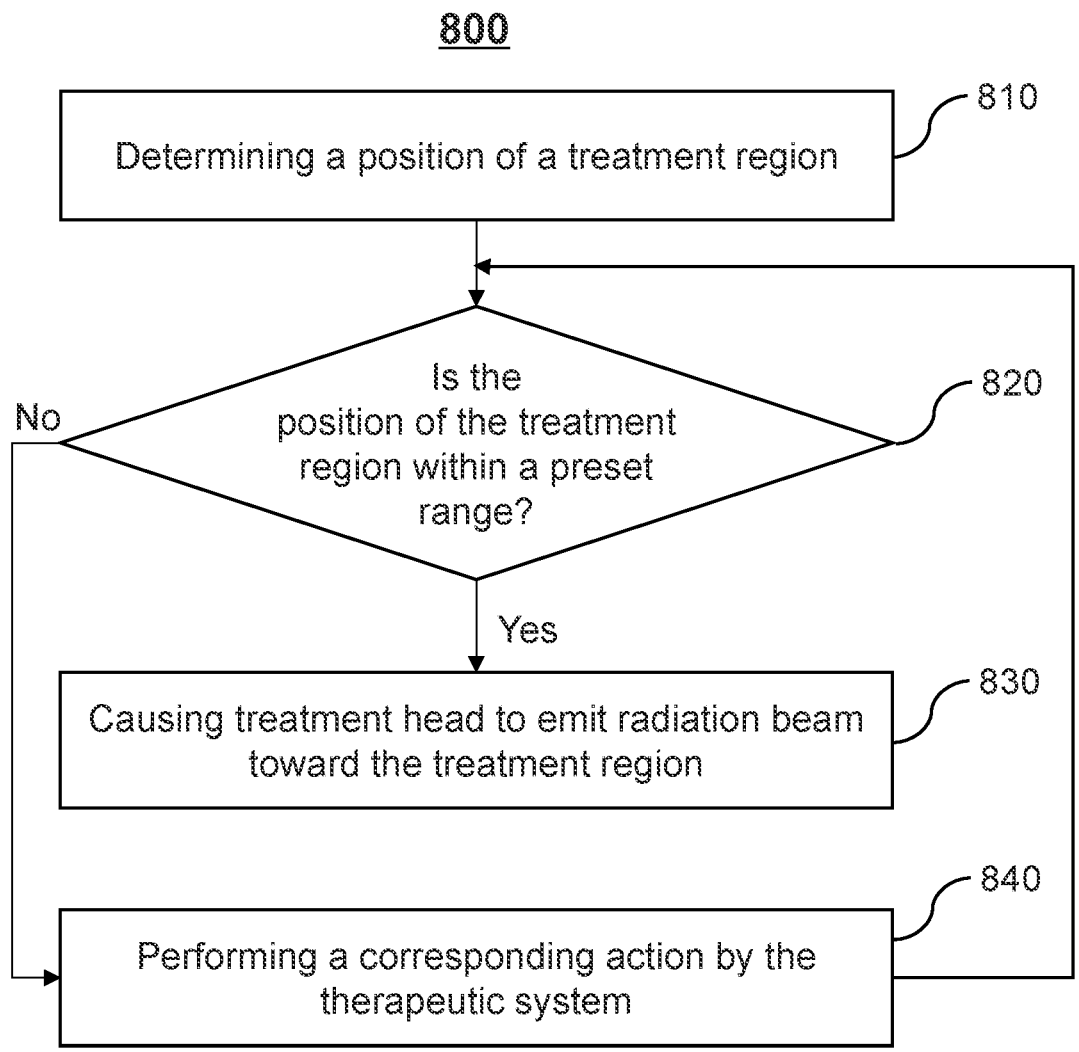
FIG. 8 is a flowchart illustrating an exemplary process for using a therapeutic system according to some embodiments of the present disclosure.

FIG. 8 is a flowchart illustrating an exemplary process 800 for using a therapeutic system according to some embodiments of the present disclosure. In some embodiments, one or more operations of the process 800 illustrated in FIG. 8 may be implemented in the therapeutic system 100 illustrated in FIG. 1. For example, the process 800 illustrated in FIG. 8 may be stored in the storage device 140 in the form of instructions, and invoked and/or executed by the processing engine 120 and/or the controller 500. In some embodiments, the process 800 may also be implemented by a user.

In 810, a position of a treatment region may be determined. Operation 810 may be performed by the processing engine 120, the controller 500, or a user. In some embodiments, the treatment region may be a cancerous tumor or lesion. The position of the treatment region may be determined by the MRI device 200 as described in FIG. 3 and/or FIG. 6.

In 820, a judgment may be made as to whether the position of the treatment region is within a preset range. Operation 820 may be performed by the processing engine 120, the controller 500, or a user. In some embodiments, the judgment may be conducted by using the MRI device 200. For example, the MRI device 200 may generate MRI images in real time to determine a current position of the treatment region. For example, by registering the MRI image and an initial MRI image, the information regarding the movement of the treatment region may be obtained. In some embodiments, the preset range may be determined in the treatment plan as described in connection with FIG. 3.

If the position of the treatment region is within the preset range, the process 800 may proceed to 830. In 830, the radiation beam may be emitted toward the treatment region. Operation 830 may be performed by the processing engine 120, the controller 500, or a user. For example, when the treatment head 310 is at the suitable place, the processing 120, the controller 500, and/or the user may cause the treatment head 310 to emit a radiation beam toward the treatment region to carry out a treatment.

If the position of the treatment region is not within the preset range, the process 800 may proceed to 840. In 840, a corresponding action may be performed by the therapeutic system 100. In some embodiments, operation 840 may be performed by the processing engine 120, the controller 500, or a user.

In some embodiments, the corresponding action may include adjusting the position of the platform 410 and/or the treatment head 310. For example, the controller 500 may cause the platform 410 to move such that the position of the treatment region is located within the preset range (e.g., the axis 370 of the radiotherapy device 300). As another example, the treatment head 310 may be adjusted to make the relative distance between the treatment head 310 and the treatment region is same with their former relative distance. As still another example, an adjusting angle may be determined according to the position of the treatment region and the position of the treatment head 310. The controller 500 may cause the treatment head 310 to rotate along the recess 202 of the magnetic body 210 according to the adjusting the adjusting angle. Detailed description may be found elsewhere in the present disclosure. See, for example, FIG. 9.

In some embodiments, the corresponding action may include stopping the treatment head 310 from emitting the radiation beam toward the treatment region. For example, the treatment head 310 may keep emitting the radiation beam before operation 840; in response to the determination that the treatment region is not within a preset range, the treatment head 310 may halt the emission. In some embodiments, the emission may resume when the treatment region is adjusted to be positioned in the preset range. In these embodiments, the MRI device 200 may act as a gating device to control the emission from the treatment head 310.

In some embodiments, the corresponding action may include modifying a treatment plan. For example, if the movement of the treatment region is huge, the process 800 may be terminated and the treatment plan may be modified according to the movement.

Then the process 800 may proceed to 820 again to judge whether the position of the treatment region is within a preset range. In some embodiments, the process 800 may be performed iteratively.

It should be noted that the above description of the process 800 is merely provided for the purpose of illustration, and not intended to limit the scope of the present disclosure. For persons having ordinary skills in the art, multiple variations and modifications may be made to the process 800 under the teachings of the present disclosure. However, those variations and modifications do not depart from the scope of the present disclosure. For example, the position of the treatment region in operation 810 may also be determined by a CT device, a PET device, etc.

Figure 9:
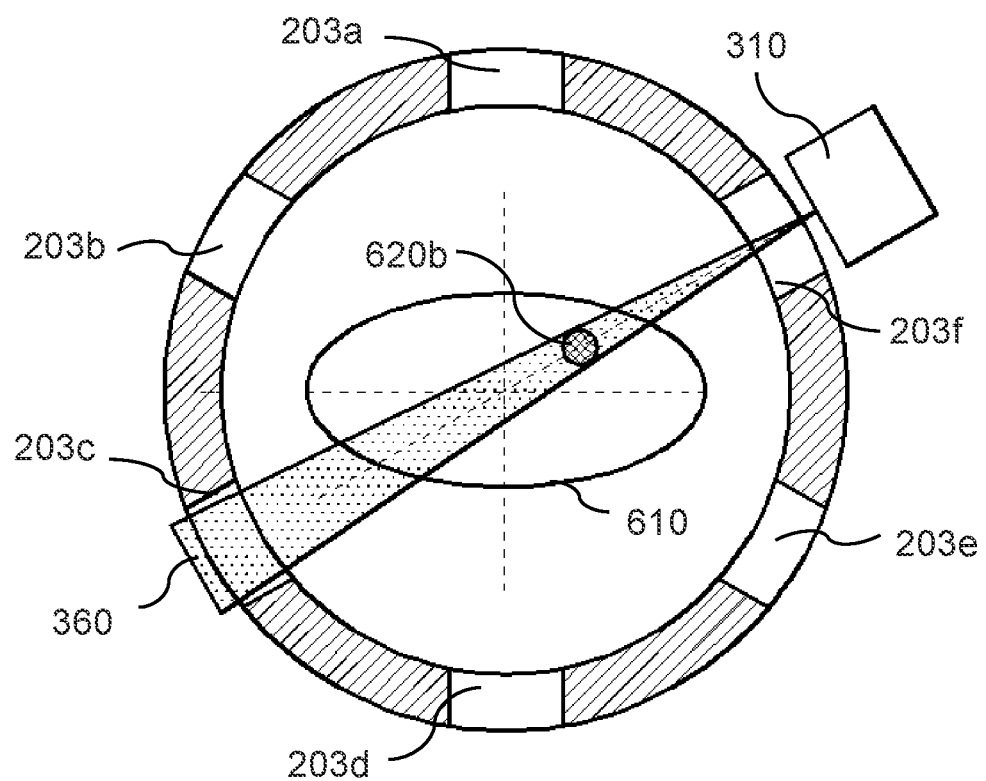
FIG. 9 shows a cross-sectional view of some components of an exemplary therapeutic apparatus according to some embodiments of the present disclosure.

FIG. 9 shows a cross-sectional view of some components of an exemplary therapeutic apparatus 110 according to some embodiments of the present disclosure. As illustrated in FIG. 9, a treatment region 620b may depart from the center (or the axis 211) of the bore 201 during a treatment. The parameters of the radiation beam 360 may be dynamically adjusted based on a position of the treatment region 620b determined based on an MR image acquired shortly before or during a treatment. For example, such an MR image may be acquired less than 1 day, or half a day, or 6 hours, or 3 hours, or 1 hour, or 45 minutes, or 30 minutes, or 20 minutes, or 15 minutes, or 10 minutes, or 5 minutes, etc., before the treatment head 310 starts emitting a radiation beam for treatment based on an original treatment plan or an adjusted treatment plan (e.g., an original treatment adjusted based on the acquired MR image). The adjustment may be achieved by adjusting one or more parameters or configuration of the treatment head 310, the platform 410, or the like, or a combination thereof. For example, the irradiating angle may be adjusted when the position of the treatment region 620b has changed. As another example, the MLC of the treatment head 310 may be adjusted to adjust the irradiating angle, the irradiating area, etc., of the radiation beam 360. As a further example, the position of the platform 410 may be adjusted so as to position the tumor on the center (or the axis 211) of the bore 201 (e.g., along the axis 370 of the radiotherapy device 300). If there is no change or the change is insignificant, the treatment region 620b may still be within the range of the radiation beam 360. The sixth opening 203a at the bottom of the recess 202 may allow radiation beams emitted by the treatment head 310 to pass through to reach the treatment region 620a without substantial attenuation. The radiation source 311 may be closer to the target treatment region 620b, because of the recess 202 in the outer wall of the magnetic body 210. The reduction in the distance between the treatment head 310 and the axis 211 of the bore 201 may bring about an increase of the radiation dose arriving at the treatment region 620b and/or an enhancement in the therapeutic efficiency.

Figure 10:
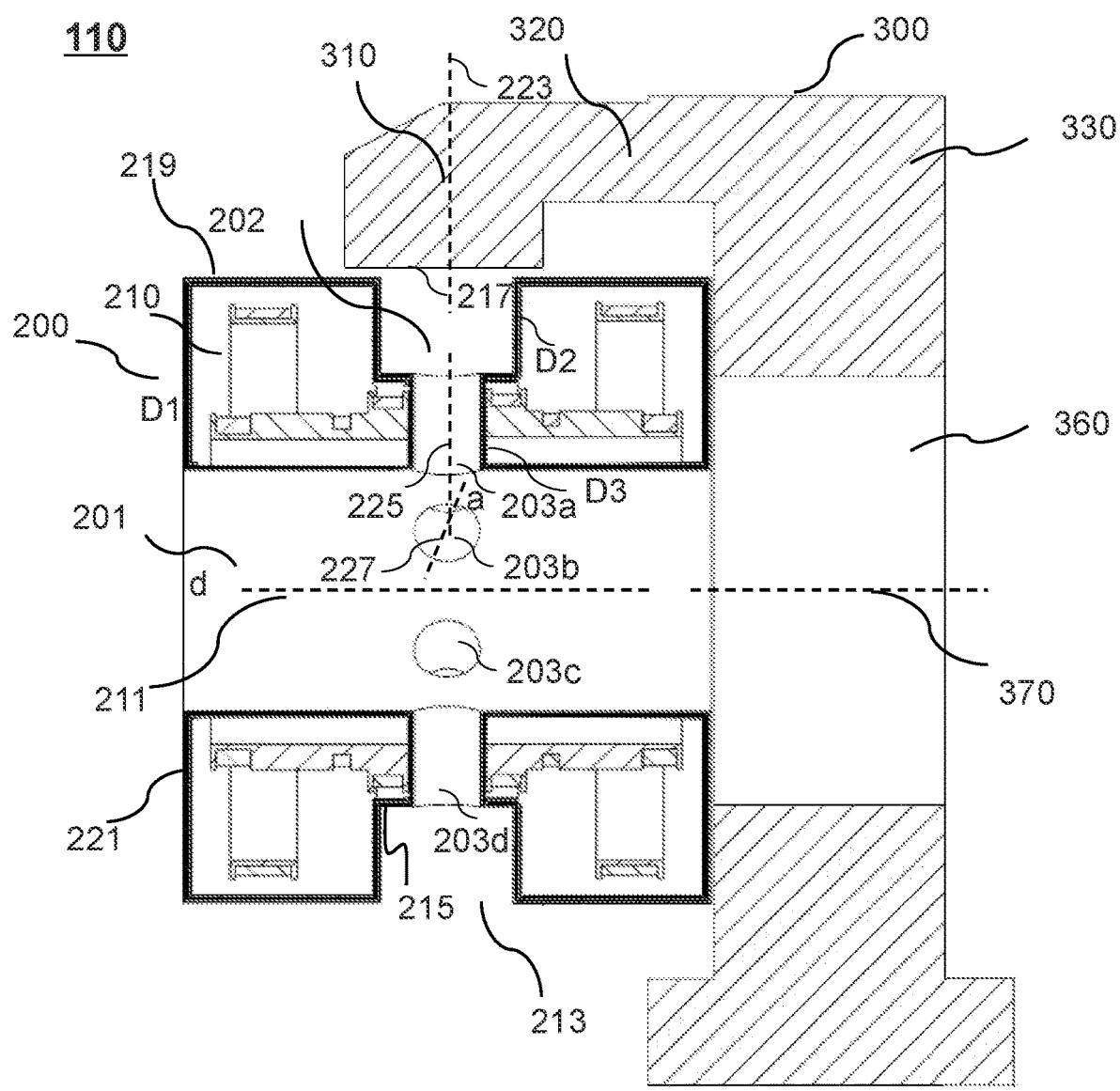
FIG. 10 shows an exemplary therapeutic apparatus according to some embodiments of the present disclosure.

FIG. 10 shows a cross-sectional view of an exemplary therapeutic apparatus 110 according to some embodiments of the present disclosure. Like reference numerals in FIGS. 4 and 10 represent like structural components, the description of which may be found in the description of FIG. 4 and/or elsewhere in the present disclosure and therefore are not repeated here. As illustrated in FIG. 10, the treatment head 310 is placed above the recess 202, thereby reducing interference to the magnetic field by the treatment head 310, compared with the configuration of the treatment head being at least partially within the recess 202 as illustrated in FIG. 4. This arrangement illustrated in FIG. 10 may obviate the need to provide a shielding device on the treatment head, thereby simplifying the structural complexity of the therapeutic apparatus 110. In some embodiments, the reduction in the interference to the magnetic field may bring about an increase of imaging quality of a treatment region (e.g., a tumor) of a subject imaged and/or treated in the therapeutic apparatus 110. As shown in FIG. 10, a top area 213 of the recess 202 may be equal to a bottom area 215 of the recess 202.

Figure 11:
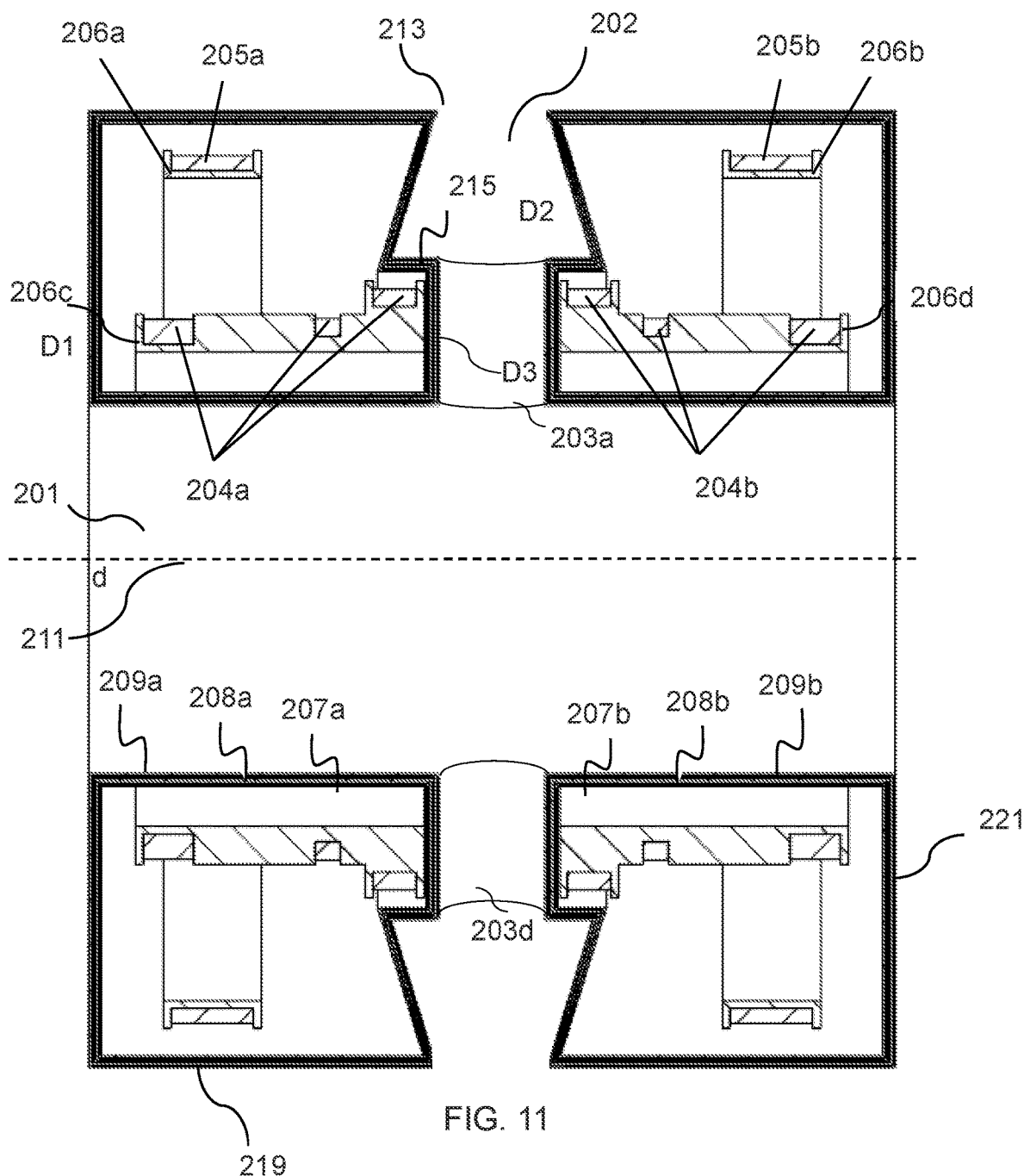
FIG. 11 shows a cross-sectional view of an exemplary magnetic body according to some embodiments of the present disclosure.

FIG. 11 shows a cross-sectional view of an exemplary magnetic body 210 according to some embodiments of the present disclosure. Like reference numerals in FIGS. 5, 10, and 11 represent like structural components, the description of which may be found in the description of FIGS. 5 and 10, and/or elsewhere in the present disclosure and therefore are not repeated here. As shown in FIG. 11, a top area 213 of the recess 202 may be less than a bottom area 215 of the recess 202. In some embodiments, by controlling the movement (e.g., rotation) of the gantry 330 by the controller 500, the treatment head 310 may rotate above the recess 202 of the magnetic body 210. For example, during a treatment, by rotating the gantry 330, a radiation beam from the treatment head 310 may be directed toward a treatment region at any angle between the radiation beam and the subject (e.g., 0 degrees, 15 degrees, 30 degrees. 60 degrees, 120 degrees).

The system illustrated in FIGS. 10 and 11 may include a first device 300 and a second device 200. The first device 300 may include a treatment head 310 configured to emit a radiation beam. The second device 200 may include a cylindrical body 221.

In some embodiments, the cylindrical body 221 may include a recess 202 on an outer wall 219 of the cylindrical body 221. The treatment head 310 may be located above the outer wall 219 of the cylindrical body 221. In some embodiments, the cylindrical body 221 may include one or more openings 203 that allow passage of the radiation beam substantially free of interference by the cylindrical body 221. The one or more openings 203 may be located at a bottom 215 of the recess 202.

In some embodiments, the system may include a controller configured to cause the treatment head 310 to rotate along the recess 202 and be located at or pass through one or more positions corresponding to the one or more openings 203. In some embodiments, the controller may be configured to cause an axis 223 of the treatment head 310 to match an axis of an opening (e.g., axis 225 of the opening 203a illustrated in FIG. 10) of the one or more openings 203 at the bottom 215 of the recess 202.

In some embodiments, the system may include a bore 201 along the axis 211 of the second device 200. The depth D2 along the radial direction of the cylindrical body 221 of the recess 202 may be determined based on an external diameter D1 of the cylindrical body 221, an inner diameter d of the cylindrical body 221, and an irradiating distance of the treatment head 310. In some embodiments, the irradiating distance may relate to a distance between an end face 217 of the treatment head 310 and an axis 211 of the cylindrical body 221.

In some embodiments, the depth D3 along the radial direction of the cylindrical body 221 of at least one of the one or more openings 203 may be determined according to the external diameter U of the cylindrical body 221, the inner diameter d of the cylindrical body 221, and the depth D2 of the recess 202.

In some embodiments, a top area 213 of the recess 202 on the outer wall 219 of the cylindrical body 221 may be equal to a bottom area 215 of the recess 202, as illustrated in FIG. 10. In some embodiments, the top area 213 of the recess 202 on the outer wall 219 of the cylindrical body 221 may be less than the bottom area 215 of the recess 202, as illustrated in FIG. 11. In some embodiments, the bottom area 215 may increases as the bottom of the recess 202 approaches the axis 211 of the cylindrical body 221. In some embodiments, the bottom area 215 of the recess 202 may be equal to area of the one or more openings. In some embodiments, the recess 202 may not block transmission of the treatment beam.

In some embodiments, the one or more openings 203 may be uniformly distributed along the recess 202. In some embodiments, an angle between axes of each pair of two adjacent openings (e.g., angle a between axes of two adjacent openings 203a and 203b) of the one or more openings 203 may be, e.g., 180 degrees, 120 degrees, 90 degrees, 60 degrees, or 30 degrees. In some embodiments, the shapes of the one or more openings 203 may be at least one of a rectangle, a rounded rectangle, a circle, an ellipse, a rhombus, a polygon, or a rounded polygon. In some embodiments, at least one of the one or more openings 203 may correspond to an arc of a circumference of the recess 202. In some embodiments, at least one of the one or more openings may include a through hole. In some embodiments, at least one of the one or more openings may be filled up by a material that is at least partially radiation transparent.

In some embodiments, the first device 300 of the system as illustrated in FIGS. 10 and 11 may include a radiotherapy device. In some embodiments, the second device 200 of the system as illustrated in FIGS. 10 and 11 may include a magnetic resonance imaging device.

In some embodiments, the cylindrical body 221 may include a magnetic body 210 configured to generate a magnetic field. In some embodiments, the magnetic body 210 may include one or more main coils that are electrically connected to each other.

In some embodiments, a method of using the system as illustrated in FIGS. 10 and 11 may include at least one of the following operations. A position of a treatment region of a subject may be determined. The position of the treatment region may be determined to be within a preset range of the system (e.g., a working area for imaging (or referred to as an imaging area) in the system, a working area for treatment (or referred to as a treatment area) in the system, an overlap area of the imaging area and the treatment area). The treatment head 310 may be caused to emit a radiation beam toward the treatment region.

In some embodiments, if it is determined that the position of the treatment region is outside the preset range, the position of the treatment region of the subject may be adjusted so that the treatment region is positioned according to the preset range. For instance, an adjusting angle of the treatment head 310 may be determined based on the position of the treatment region so that the treatment head 310 may be adjusted according to the adjusting angle.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," "or system." Furthermore, aspects of the present disclosure may take the form of a computer program product embodied in one or more computer readable media having computer readable program code embodied thereon.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques, Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system comprising:
a first device including a treatment head configured to emit a radiation beam;
a second device comprising a cylindrical body, wherein the cylindrical body comprises a recess on an outer wall of the cylindrical body, wherein an end face of the treatment head, from which the radiation beam is emitted, is located above the recess and outside the recess.

2. The system of claim 1, wherein the cylindrical body further includes a plurality of openings, wherein each of the plurality of openings corresponds to an opening at an opposite position on the recess, and the plurality of openings are at a bottom of the recess.

3. The system of claim 2, further comprising:
a controller configured to cause the treatment head to rotate around a magnetic resonance imaging device included in the second device and be located at or pass through a plurality of positions corresponding to the plurality of openings.

4. The system of claim 3, wherein the controller is further configured to cause an axis of the treatment head to match an axis of an opening of the plurality of openings at the bottom of the recess.

5. The system of claim 2, wherein a top area of the recess on the outer wall of the cylindrical body is less than a bottom area of the recess.

6. The system of claim 2, wherein the plurality of openings are uniformly distributed along the recess.

7. The system of claim 6, wherein an angle between axes of each pair of two adjacent openings of the plurality of openings is 180 degrees, 120 degrees, 90 degrees, 60 degrees, or 30 degrees.

8. The system of claim 2, wherein shapes of the plurality of openings include at least one of a rectangle, a rounded rectangle, a circle, an ellipse, a rhombus, a polygon, or a rounded polygon.

9. The system of claim 2, wherein at least one of the plurality of openings has a shape of an arc of a circumference of the recess.

10. The system of claim 2, wherein at least one of the plurality of openings is a through hole.

11. The system of claim 10, wherein at least one of the plurality of openings is filled up by a material that is at least partially radiation transparent.

12. The system of claim 1, further comprising a bore along an axis of the second device, wherein a depth along a radial direction of the cylindrical body of the recess is determined according to an external diameter of the cylindrical body, an inner diameter of the cylindrical body, and an irradiating distance of the treatment head.

13. The system of claim 12, wherein the irradiating distance relates to a distance between the end face of the treatment head and an axis of the cylindrical body.

14. The system of claim 12, wherein the cylindrical body further includes a plurality of openings, wherein a depth along the radial direction of the cylindrical body of at least one of the plurality of openings is determined according to the external diameter of the cylindrical body, the inner diameter of the cylindrical body, and the depth of the recess.

15. The system of claim 1, the first device including a radiotherapy device.

16. The system of claim 1, the cylindrical body including a magnetic body configured to generate a magnetic field.

17. The system of claim 16, the magnetic body further including more main coils that are electrically connected to each other.

18. A method of using a system comprising a first device and a second device, wherein the first device includes a treatment head configured to emit a radiation beam, the second device includes a cylindrical body, and the cylindrical body comprises a recess on an outer wall of the cylindrical body, wherein an end face of the treatment head, form which the radiation beam is emitted, is located above the recess and outside the recess, the method comprising:
 determining a position of a treatment region of a subject;
 determining that the position of the treatment region is within a preset range; and
 causing the treatment head to emit the radiation beam toward the treatment region.

19. The method of claim 18, further comprising:
 determining that the position of the treatment region is not within the preset range; and
 adjusting the position of the treatment region according to the preset range.

20. The method of claim 18, further comprising:
 determining that the position of the treatment region is not within the preset range;
 determining, based on the position of the treatment region, an adjusting angle of the treatment head; and
 rotating the treatment head according to the adjusting angle.

* * * * *